United States Patent
Sisti et al.

[19]

[11] Patent Number: 6,107,497

[45] Date of Patent: Aug. 22, 2000

[54] INTERMEDIATE FOR USE IN DOCETAXEL SYNTHESIS AND PRODUCTION METHOD THEREFOR

[75] Inventors: Nicholas J. Sisti, Pepperrell, Mass.; Charles S. Swindell, Merion, Pa.; Madhavi C. Chander, Boulder, Colo.

[73] Assignees: NaPro BioTherapeutics, Inc., Boulder, Colo.; Bryn Mawr College, Bryn Mawr, Pa.

[21] Appl. No.: 08/616,466

[22] Filed: Mar. 19, 1996

Related U.S. Application Data

[63] Continuation-in-part of application No. 08/609,083, Feb. 29, 1996, abandoned.

[51] Int. Cl.$^7$ .................................................. C07D 305/14
[52] U.S. Cl. ........................................... 549/510; 549/511
[58] Field of Search ....................... 549/510, 511

[56] References Cited

U.S. PATENT DOCUMENTS

| | | | |
|---|---|---|---|
| Re. 34,277 | 6/1993 | Denis et al. | 549/510 |
| 4,814,470 | 3/1989 | Colin et al. | 514/449 |
| 4,924,011 | 5/1990 | Denis et al. | 549/510 |
| 4,924,012 | 5/1990 | Colin et al. | 549/510 |
| 5,015,744 | 5/1991 | Holton | 549/510 |
| 5,136,060 | 8/1992 | Holton | 549/510 |
| 5,399,726 | 3/1995 | Holton et al. | 549/510 |

FOREIGN PATENT DOCUMENTS

| | | |
|---|---|---|
| 0400971 | 5/1990 | European Pat. Off. . |
| 0528729A1 | 2/1993 | European Pat. Off. . |
| WO93/16060 | 8/1993 | WIPO . |

OTHER PUBLICATIONS

Greene et al, "Protective groups in Organic Synthesis", $2^{nd}$ ed, 1991, pp. 10–13.

"Taxol Photoaffinity Label: 7–(p–Azidobenzoyl)taxol Synthesis and Biological Evaluation", Georg et al, *Biorganic & Medicinal Chemistry Letters,* vol. 2, No. 7, pp. 735–738, 1992.

*Primary Examiner*—Ba K. Trinh
*Attorney, Agent, or Firm*—Timothy J. Martin; Michael R. Henson; Mark H. Weygandt

[57] ABSTRACT

C7, C10 di-CBZ 10-deacetyl baccatin III of the formula:

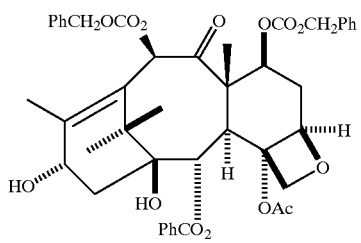

provides an intermediate for the production of docetaxel. A method of producing this C7, C10 di-CBZ 10-deacetyl Baccatin III is provided. Here, 10-deacetyl Baccatin III is acylated with at least 1.5 equivalents of n-butyl lithium and at least 1.5 equivalents of benzyl chloroformate in tetrahydrofuran. The 10-deacetyl Baccatin III may first be dissolved in tetrahydrofuran after which the n-butyl lithium is added followed by the addition of the benzyl chloroformate. The reaction is preferably at a reduced temperature of less than −20° C. The resulting solution may be quenched with ammonium chloride and reduced to residue. The residue may then be redissolved in an organic solvent, washed, dried and recrystallized to purify the compound.

12 Claims, No Drawings

INTERMEDIATE FOR USE IN DOCETAXEL SYNTHESIS AND PRODUCTION METHOD THEREFOR

RELATED APPLICATION

This application is a continuation-in-part of our earlier application, Ser. No. 08/609,083, filed Feb. 29, 1996 and entitled Intermediate For Docitaxel Synthesis and Production Method Therefor, now abandoned.

FIELD OF THE INVENTION

This invention generally relates to the synthesis of docetaxel from precursor compounds. More particularly, though, this invention concerns the synthesis of docetaxel using a suitably protected 10-deactyl Baccatin III backbone which is esterified with a suitably protected side chain acid to produce an intermediate that may thereafter be deprotected, acylated and further deprotected to produce docetaxel.

BACKGROUND OF THE INVENTION

Various taxane compounds are known to exhibit anti-tumor activity. As a result of this activity, taxanes have received increasing attention in the scientific and medical community. Primary among these is a compound known as "paclitaxel" which is also referred to in the literature as "taxol". Paclitaxel has been approved for the chemotherapeutic treatment of several different varieties of tumors, and the clinical trials indicate that paclitaxel promises a broad range of potent anti-leukemic and tumor-inhibiting activity.

Paclitaxel is a naturally occurring taxane diterpenoid which is found in several species of the yew (genus Taxus, family Taxaceae). Unfortunately, the concentration of this compound is very low. The species of evergreen are also slow growing. Even though the bark of the yew trees typically exhibit the highest concentration of paclitaxel, the production of one kilogram of paclitaxel requires approximately 16,000 pounds of bark. Thus, the long term prospects for the availability of paclitaxel through isolation is discouraging.

While the presence of paclitaxel in the yew tree is in extremely low concentrations, there are a variety of other taxane compounds, such as Baccatin III, cephalomanine, 10-deacetylbaccatin III, etc., which are also able to be extracted from the yew bark. Some of these other taxane compounds are more readily extracted in higher yields. Indeed, a relatively high concentration of 10-deacetylbaccatin III can be extracted from the leaves of the yew as a renewable resource.

Among the various taxane compounds which have been found to exhibit anti-tumor activity is the compound known as "docetaxel". This compound is also sold under the trademark TAXOTERE® by Rhone-Poulenc Sante. Docetaxel has the formula as follows:

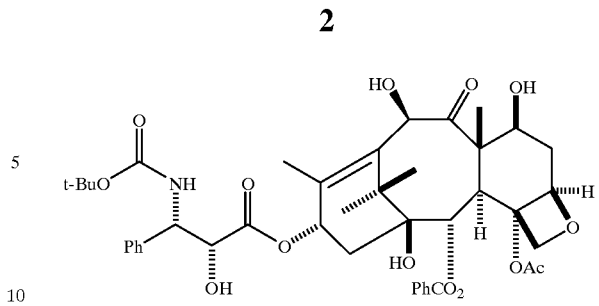

As may be seen in this formulation, docetaxel is similar to paclitaxel except for the inclusion of the t-butoxycarbonyl (t-BOC) group at the C3' nitrogen position of the isoserine side chain and a free hydroxy group at the C10 position. Several possible syntheses of docetaxel and related compounds have been reported in the *Journal of Organic Chemistry:* 1986, 51, 46; 1990, 55, 1957; 1991, 56, 1681; 1991, 56, 6939; 1992, 57 4320; 1992, 57 6387; and 1993, 58, 255.

In order to successfully synthesize docetaxel, convenient access to a chiral, non-racemic side chain and an abundant natural source of a usable baccatin III backbone as well as an effective means of joining the two is necessary. However, the esterification of the side chain to the baccatin III backbone is difficult because of the hindered C13 hydroxyl in the baccatin III backbone which is located within the concave region of the hemispherical taxane skeleton. This difficulty of synthesis is present both for the synthesis of docetaxel as well as for the synthesis of paclitaxel.

One technique for the semi-synthesis of paclitaxel is found in co-pending patent application Ser. No. 08/483,081. In this application, paclitaxel is synthesized from C7 TES protected baccatin III with N-carbamate protected C2' hydroxyl-benzyl protected (2R,3S)-3-phenyl isoserine A-ring side chain with a hydrogenable benzyl-type protecting group, such as a benzyloxymethyl (BOM) protecting group at the C2' location for the side chain. Following the condensation of the C7 TES protected baccatin III and the side chain, the compound may be suitably deprotected, acylated, and further deprotected to yield paclitaxel.

While the existing techniques for synthesizing docetaxel certainly have merit, there is still a need for improved chemical processes which can produce this anti-cancer compound. The present invention is directed to such a procedure utilizing the N-carbamate protected C2' hydroxyl benzyl protected (2R,3S)-3-phenylisoserine A-ring side chain as described in my earlier co-pending application.

SUMMARY OF THE INVENTION

It is an object of the present invention to provide a new, useful and efficient protocol for the attachment of a protected A-ring side chain to a protected baccatin III skeleton which may then be converted into docetaxel.

Another object of the present invention is to provide a new compound in the form of a suitably protected baccatin III backbone which can be used in the semi-synthesis of docetaxel as well as a method for producing such compound.

It is still a further object of the present invention to provide a new and useful protocol for the semi-synthesis of docetaxel in an effort to produce a high yield of docetaxel in a cost efficient manner.

Yet another object of the present invention is to provide a method for the production of docetaxel which potentially can be scaled to commercial implementation.

According to the present invention, then, a new and useful chemical compound is disclosed having the formula:

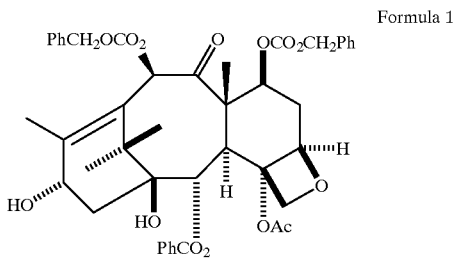

Formula 1

The present invention is also directed to method of producing this compound by acylating 10-deacetylbaccatin III with at least 1.5 equivalents of n-butyl lithium and at least 1.5 equivalents of benzyl chloroformate and tetrahydrofuran. According to the present invention, docetaxel is produced by reacting the C7, C10 dicarbobenzyloxyl 10-deacetylbaccatin III with an isoserine side chain having a general formula:

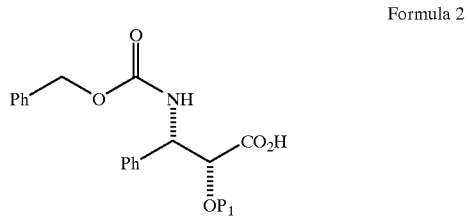

Formula 2

$P_1$=hydrogenable benzyl-type protecting group and thereafter deprotecting the coupled product at C7 and at C10 and at the C3' nitrogen site. Next, the side chain nitrogen is acylated to add the t-butoxycarbonyl group (t-BOC) at the C3' nitrogen side chain site. Thereafter, suitable deprotection is obtained to remove the protecting group at C2' to produce docetaxel.

Preferably, the method of producing C7, C10 dicarbobenzyloxy 10-deacetylbaccatin III is accomplished by dissolving 10-deacetylbaccatin III in tetrahydrofuran to form a solution after which at least 1.5 equivalents, but preferably 2 equivalents, of n-butyl lithium is added to form a first mixture and, thereafter, at least 1.5 equivalents, but preferably 2 equivalents, of benzylchloroformate is added to the first mixture to a form a second mixture. The second mixture may be quenched with ammonium chloride solution and thereafter reduced to a residue. This residue may then be dissolved in an organic solvent that is not miscible in water to form a residue solution after which the residue solution is washed with water and thereafter with brine to form an organic layer. The organic layer may then be removed, dried and recrystallized or chromatographed, preferably with ethyl acetate/hexane.

In the preferred method, the reactions are at a reduced temperature of −20° C. or less. Here, the solution of 10-deacetylbaccatin III in tetrahydrofuran is lowered to the reduced temperature which is preferably about −78° C. After the n-butyl lithium in hexane is added dropwise to this solution to form the first mixture, the first mixture is stirred at the reduced temperature for approximately five minutes. Benzylchloroformate is then added to the first mixture at the reduced temperature to form the second mixture, and the second mixture is stirred for approximately one hour at a reduced temperature of no more than 0° C.

These and other objects of the present invention will become more readily appreciated and understood from a consideration of the following detailed description of the exemplary embodiments.

DETAILED DESCRIPTION OF THE EXEMPLARY EMBODIMENTS

The present disclosure is broadly directed to a chemical process for the efficient production of docetaxel as well as intermediate and precursors therefor. More specifically, the present invention discloses a new chemical compound in the form of C7, C10-di-CBZ 10-deacetylbaccatin III as a useful intermediate in the production of docetaxel. The C7, C10-di-CBZ 10-deacetylbaccatin III is esterified with a 3-phenylisoserine acid having a hydrogenable benzyl protecting group at C2' to the C13 hydroxyl of the baccatin III backbone. The general process described herein involves the production of the C7, C10-di-CBZ 10-deacetylbaccatin III backbone, the production of the suitably protected 3-phenylisoserine acid having the hydrogenatable benzyl-type protecting group C2', the condensation of the two compounds, and the subsequent deprotection, acylation at the C3' nitrogen site to add the t-butoxycarbonyl group, followed by further deprotection to yield docetaxel.

A. Production of C7, C10 dicarbobenzyloxy 10-deacetylbaccatin III

C7, C10 di-CBZ 10-deacetylbaccatin III (Formula 1) is produced by the following reaction:

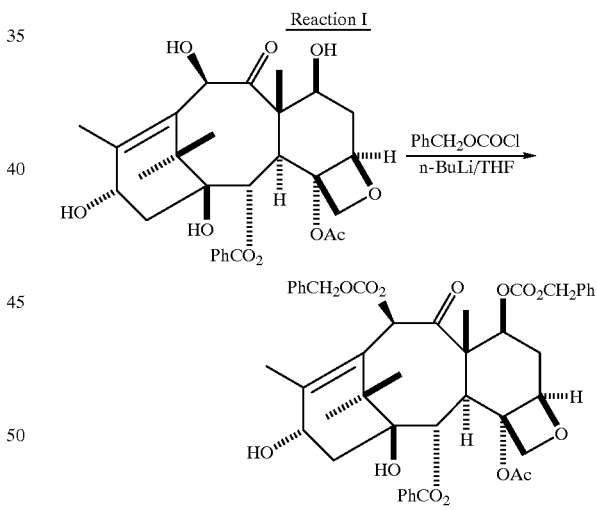

Reaction I

Here, 10-deacetylbaccatin III is dissolved in anhydrous THF (tetrahydrofuran) and is cooled under a nitrogen atmosphere to a temperature of less than −20° C. but preferably −78° C. n-butyl lithium (1.6 M in hexane) is added dropwise and the solution is stirred at the reduced temperature for approximately five minutes. At least 1.5 equivalents of n-butyl lithium are needed to get significant product yield, however 2 equivalents are preferable. Benzyl chloroformate is then added dropwise (again, at least 1.5 equivalents of the benzyl chloroformate are needed for significant yield, but 2 equivalents are preferred) and the mixture is stirred over a period of one hour during which time it is allowed to warm to a temperature of no more than 0° C. The mixture is then quenched with cold saturated ammonium chloride to eliminate any excess n-butyl lithium and acetyl chloride, and the mixture is reduced under vacuum. The residue is taken up in ethyl acetate and washed once with water and then with brine to remove unwanted salts. The organic layer may then be dried and reduced under vacuum, and the residue recrystallized or column chromotagraphed with ethyl acetate/hexane to yield C7, C10 di-CBZ 10-deacetylbaccatin III as a white solid in greater than 80% overall yield.

B. Production of the 3-Phenylisoserine Side Chain

The production of the (2R,3S) N-CBZ C2' 0-protected 3-phenylisoserine ethyl ester side chain, where the C2' hydroxy group is protected by a hydrogenatable benzyl-type protecting group (Formula 2), can be accomplished from the starting compound (2R, 3S) 3-phenylisoserine ethyl ester according to the following two reactions. The first reaction is:

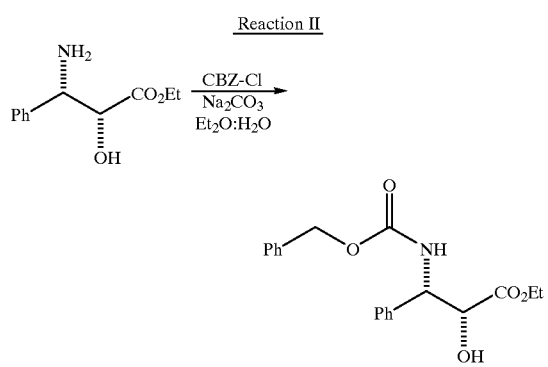

Here, (2R, 3S) 3-phenylisoserine ethyl ester was alternatively dissolved in either equal parts diethyl ether:water or equal parts methyl t-butyl ether:water and the solution was cooled to 0° C. The sodium carbonate was then added to the solution and benzylchloroformate was added dropwise over an interval of about five minutes and the resulting mixture stirred at 0° C. for approximately one hour. After the one hour stirring, the solution was then poured into water and extracted with methylene chloride or ethyl acetate, as desired. The organic layer is separated, dried and reduced under vacuum to residue. The residue was then recrystallized from ethyl acetate:hexane to result in N-CBZ 3-phenylisoserine ethyl ester.

This intermediate was next protected by the hydrogenatable benzyl-type protecting group in several ways. For example, one route to the desired hydrogenatable benzyl-type protected side chain is as follows:

Reaction III

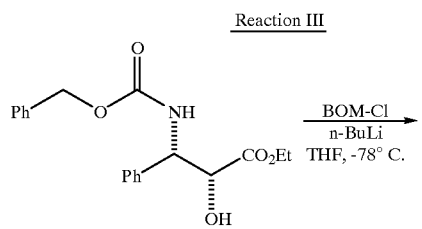

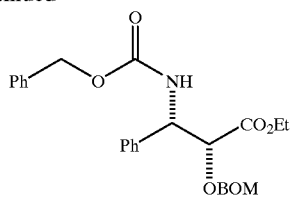

Here, the hydrogenable benzyl-type protecting group is benzyloxymethyl (BOM). To prepare this compound, the N-CBZ 3-phenylisoserine ethyl ester is dissolved in anhydrous THF under a nitrogen atmosphere and cooled to a reduced temperature such as −40° C. or −78° C., for example, in a dry ice/acetone bath followed by the dropwise addition of an alkyl lithium agent such as n-butyl lithium, although it is desirable that the alkyl lithium agent be a straight chain alkyl. In any event, the reaction is best done at a temperature no greater than 0° C. The resulting mixture is stirred for about ten minutes. Benzyloxymethyl chloride (BOM-Cl) is then added dropwise over an interval of about five minutes and the mixture stirred for approximately two to five hours at the reduced temperature. Thereafter, the solution is warmed to 0° C. and quenched with water to eliminate excess n-butyl lithium. The resulting mixture is reduced under vacuum to residue, and this residue is thereafter taken up in ethyl acetate and washed with water and brine to remove unwanted salts. The organic layer may then be dried and reduced under vacuum and the residue recrystallized from ethyl acetate:hexane or chromatographed with ethyl acetate:hexane to give the N-CBZ C2'-BOM 3-phenylisoserine ethyl ester.

Another route to production of N-CBZ C2'-OBOM 3-phenylisoserine ethyl ester is accomplished by dissolving the compound N-CBZ (2R,3S)-3-phenylisoserine ethyl ester in anhydrous methylene chloride. Thereafter, a tertiary amine base such as diisopropylethylamine is added along with BOM-Cl and the mix is refluxed for twenty-four hours. While this reaction route will produce N-CBZ 2'-BOM-3-phenylisoserine ethyl ester, the reaction proceeds much slower than the route discussed above, however, it may be preferred because of higher yield. Here, the compound is not purified, but rather is carried on to subsequent processing steps in crude form.

In either instance, the resulting N-CBZ C2'-OBOM (2R, 3S)-3-phenylisoserine ethyl ester, either in the purified form of the first route or in the crude form from the second route, may simply be converted to the corresponding acid by the reaction:

Reaction IV

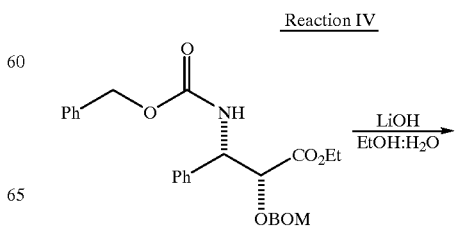

-continued

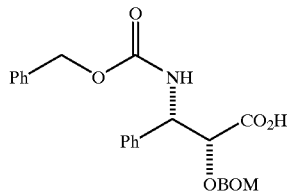

Here, the protected ethyl ester is dissolved in ethanol/water (ratio 8:1). Lithium hydroxide (or other suitable alkali hydroxide) is added to the solution and the resulting mixture stirred for approximately three hours in order to saponify the compound. The mixture is then acidified (1 N hydrochloric acid) and extracted with ethyl acetate. The resulting organic layer is separated, dried and reduced under vacuum. The residue acid is then isolated for use without further purification. This produces the desired N-CBZ C2'-OBOM (2R,3S)-3-phenylisoserine.

Where the N-CBZ C2'-OBOM 3-phenylisoserine ethyl ester is carried forward in the crude form and is converted into N-CBZ C2'-OBOM (2R,3S)-3-phenylisoserine, it is necessary for further purification of the end product. This purification is accomplished by dissolving the product in toluene followed by the dropwise addition of one equivalent dicyclohexylamine and the resulting solution is stirred for one-half hour. This mixture is then concentrated in vacuo, and the resulting residue is recrystallized from ethyl acetate-:hexane to give the dicyclohexylamine salt of the N-CBZ C2'-OBOM (2R,3S)-3-phenylisoserine. The purified N-CBZ C2'-OBOM (2R,3S)-3-phenylisoserine may then be liberated by dissolving this dicyclohexylamine salt in methylene chloride or other halogenated solvent followed by washing the methylene chloride with several portions of 1 N HCl. The organic layer is then washed with several portions of water to remove dicyclohexylamine hydrochloride. Next, it is washed with one portion of saturated brine and reduced in vacuo to give the desired acid.

Benzyl itself is another example of a hydrogenatable benzyl-type protecting group that may be used instead of BOM. N-CBZ 2'-benzyl 3-phenylisoserine ethyl ester was produced as above with the substitution of benzyl bromide for BOM-Cl according to the reaction:

Reaction V

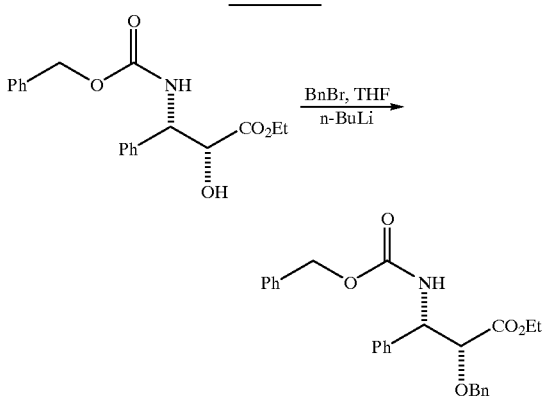

Here, the CBZ protected (2R,3S)-3-phenylisoserine ethyl ester is dissolved in anhydrous THF under a nitrogen atmosphere and cooled to a reduced temperature such as −40° C. or −78° C. for example in a dry ice/acetone bath followed by the dropwise addition of an alkyllithium agent such as n-butyl lithium, although it is desirable that the alkyllithium agent be a straight chain alkyl. The resulting mixture is stirred for about ten minutes. Benzyl bromide (BnBr) is then added dropwise over an interval of about five minutes and the mixture stirred for approximately two to five hours at the reduced temperature. Thereafter, the solution is warmed to 0° C. and quenched with water to destroy excess n-butyl lithium. The resulting mixture is reduced under vacuum to residue, and this residue is thereafter taken up in ethyl acetate and washed with water to remove any lithium bromide salt; it is then further washed with brine. The organic layer may the be dried and reduced under vacuum and the residue recrystallized from ethyl acetate:hexane or chromatographed with ethyl acetate:hexane to give N-CBZ 2'-benzyl 3-phenylisoserine ethyl ester.

Alternatively, the N-CBZ 2'-benzyl 3-phenylisoserine ethyl ester may be obtained according to the reaction:

Reaction VI

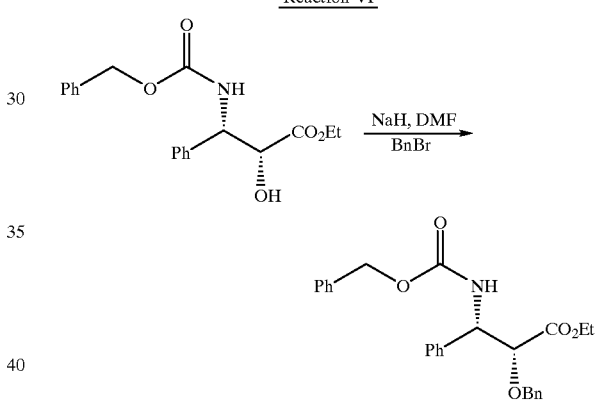

Here, to a stirred solution of NaH in anhydrous DMF under nitrogen is added N-CBZ-3-phenylisoserine ethyl ester dissolved in DMF over five minutes. The mixture is then stirred at 0° C. for one half hour. Then benzyl bromide (1.1 equivalents) is added dropwise over five minutes and the reaction is stirred for two hours. The mixture is then quenched with water to destroy excess sodium hydride. Thereafter, either diethyl ether or methyl t-butyl ether is added. The organic layer is then washed with four portions of water to remove DMF and sodium bromide. Next, it is washed with brine and then dried and reduced under vacuum to produce N-CBZ C2'-benzyl 3-phenylisoserine ethyl ester which may then be readily converted into N-CBZ C2'-benzyl 3-phenylisoserine by the process of Reaction IV above with the understanding that, in this case, benzyl is the C2' protecting group instead of benzyloxymethyl (BOM).

C. Esterification of the Protected Baccatin III with the Side Chain

Esterification of the C7, C10 di-CBZ 10-deacetylbaccatin III with the N-CBZ C2'-protected 3-phenylisoserine side chain (where the C2' hydroxyl is protected by any hydrogenatable benzyl-type group) is accomplished as follows. The preferred hydrogenatable benzyl group shown below is BOM (benzyloxymethyl).

Reaction VII

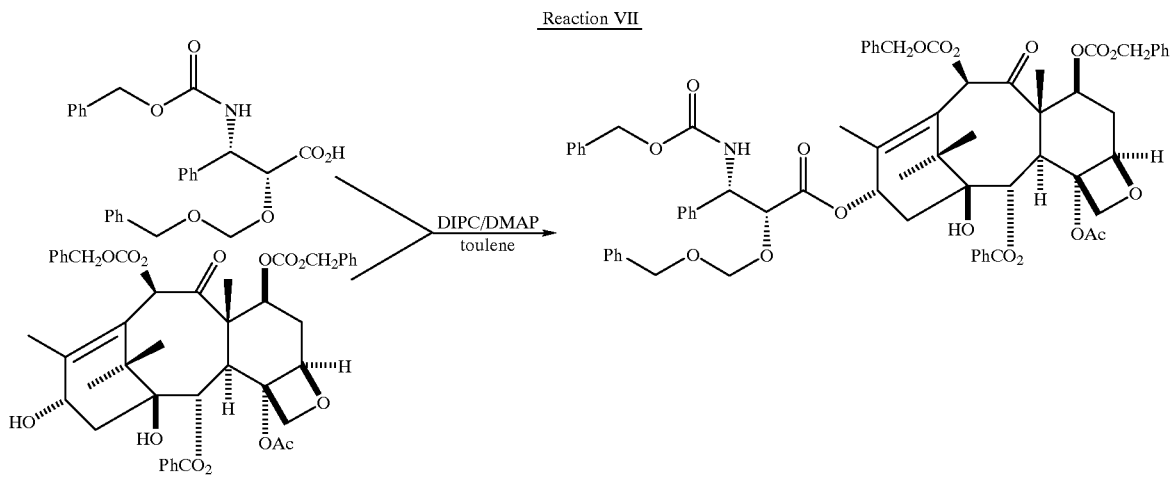

Here, the C7, C10 di-CBZ 10-deacetylbaccatin III (1 equivalent) of Formula 1 and the acid side chain (6 equivalents) of Formula 2 are dissolved in toluene. To this mixture, 4-dimethylamino pyridine (DMAP) (one equivalent) and diisopropylcarbodiimide (6 equivalents) are added, and the resulting mixture heated at about 60° C. to 80° C. for one to five hours. It should also be noted, however, that other dialkylcarbodiimides may be substituted for the diisopropylcarbodiimide, with one example being dicyclohexylcarbodiimide.

The solution is then allowed to cool to room temperature, and next an equal volume of diethyl ether is added. The resulting solution is cooled to 0° C. and held at this temperature for twenty-four hours. This step crystalizes most of the urea impurity. After the twenty-four hour interval elapses, the solution is filtered and the residue rinsed with either ethyl ether or methyl t-butyl ether. The combined organics are then washed with hydrochloric acid (5%), water, and finally brine. The organic phase is separated, dried, and reduced under vacuum. The resulting residue is then dissolved in ethyl acetate:hexane and eluted over a silica gel plug. The eluent is then reduced under vacuum to result in the desired C3' NCBZ C2'-OBOM-C7, C10-di-CBZ 10-deacetyl baccatin III of the formula:

Formula 3

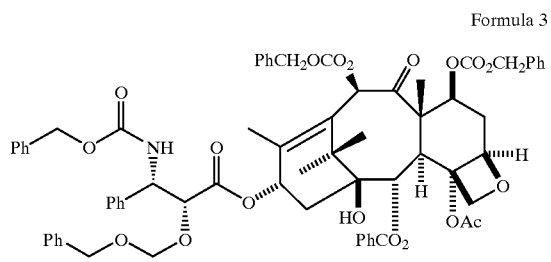

D. Deprotection and Treatment with Di-tert-Butyl dicarbonate and Deprotection to Form Docetaxel The following reaction removes the CBZ protecting groups at C7 and C10 and the C3' nitrogen side chain site. (Again for clarity, BOM is used here as an example of a C2' hydrogenatable benzyl-type protecting group):

Reaction VIII

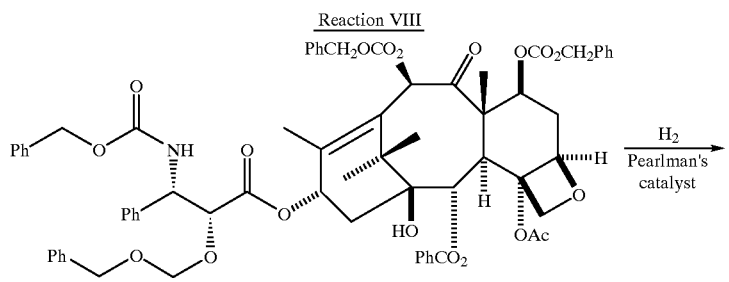

-continued

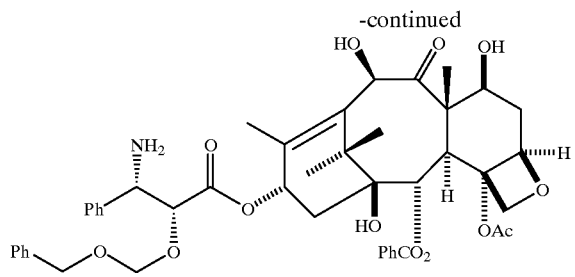

The coupled product of Formula 3 is dissolved in isopropanol/ethyl acetate to which Pearlman's catalyst is added. The resulting mixture is hydrogenated at 1 atmosphere of hydrogen for at least twenty-four hours. Thereafter, the mixture is filtered through diatomaceous earth and reduced under vacuum to residue to result in the amine shown which is used without further purification.

Next, the t-BOC group can be attached at the N-C3' side chain site according to the following reaction:

Reaction IX

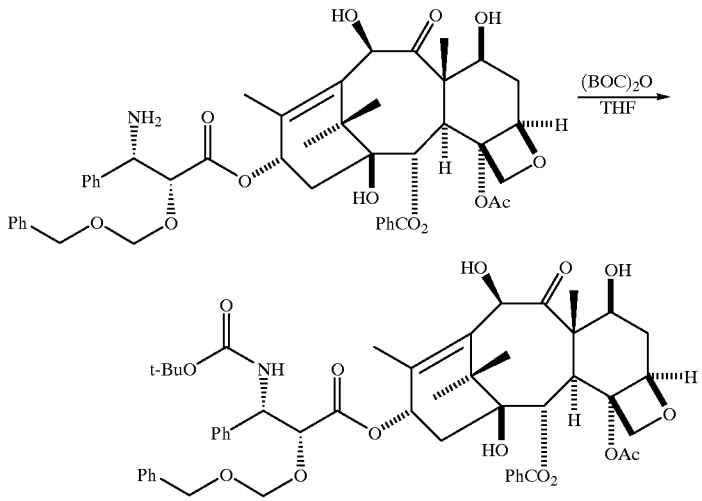

Here, the amine is taken up in anhydrous THF and a tertiary amine base may be added to accelerate the reaction, followed by the addition of di-tert-butyldicarbonate. The mixture is stirred for twenty-four hours, and then reduced under vacuum and redissolved in ethyl acetate. The organic phase was then washed with water and brine. The resulting organic phase was then separated, dried, and reduced under vacuum to get crude C2'-OBOM docetaxel. It is necessary at this stage of processing to purify the crude C2'-OBOM docetaxel. This can be accomplished by column chromatography and/or recrystalization from ethyl/acetate:hexane. Preferably both column chromatography with ethyl/acetate:hexane to produce an eluent that is reduced in vacuum to form a residue followed by recrystalization of the residue from ethyl acetate:hexane is employed to yield C2'-OBOM docetaxel in a substantially pure form.

The benzyloxymethyl protecting group is removed as follows:

Reaction X

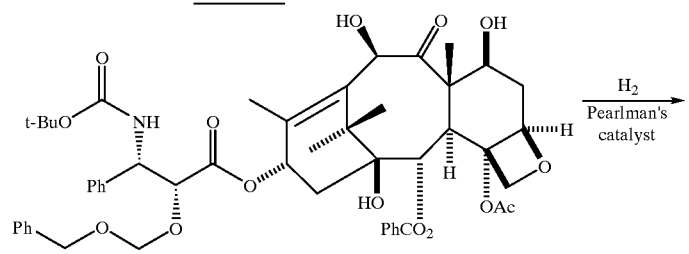

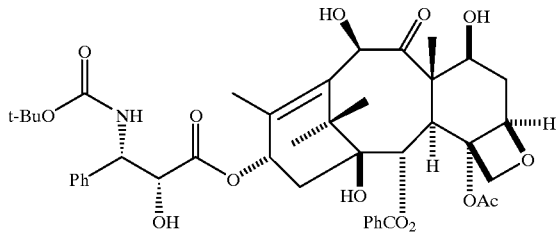

Here, the purified C2'-OBOM docetaxel is dissolved in isopropanol and Pearlmann's catalyst is added. The mixture is then hydrogenated at either 1 Atm of hydrogen or at 40 psi hydrogen for at least twenty-four hours. The mixture is then filtered through diatomaceous earth and reduced under vacuum to get crude docetaxel. Where the C2' side chain site has been protected with O-Bn, conversion to crude docetaxel may be accomplished according to the literature procedure (Kanazawa, A., Denis J. N. and Green, A. E. J. Org. Chem. 1994, 59, 1238).

Accordingly, the present invention has been described with some degree of particularity directed to the exemplary embodiment of the present invention. It should be appreciated, though, that the present invention is defined by the following claims construed in light of the prior art so that modifications or changes may be made to the exemplary embodiments of the present invention without departing from the inventive concepts contained herein.

We claim:

1. A chemical compound having the formula:

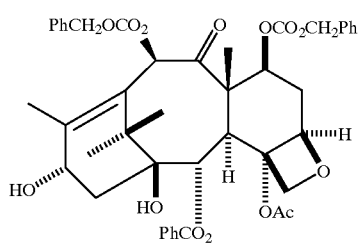

(1)

2. A method of producing a compound having the formula:

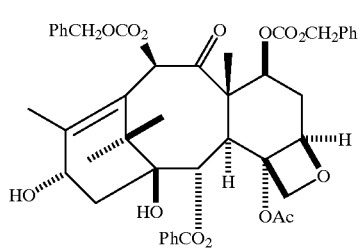

(1)

comprising the step of acylating 10-deacetyl Baccatin III with at least a 1.5 equivalents of n-butyl lithium and at least 1.5 equivalents of benzyl chloroformate in tetrahydrofuran.

3. A method according to claim 2 wherein the 10-deacetyl Baccatin III is first dissolved in said tetrahydrofuran to form a solution after which said n-butyl lithium is next added to form a first mixture and thereafter said benzyl chloroformate is added to said first mixture to form a second mixture.

4. A method according to claim 3 wherein said n-butyl lithium is in a hexane solution, said n-butyl lithium in hexane being added dropwise to said solution.

5. A method according to claim 3 wherein said solution is cooled to a reduced temperature of −20° C. or less prior to adding said n-butyl lithium.

6. A method according to claim 5 wherein the reduced temperature is about −78° C.

7. A method according to claim 5 wherein said first mixture is stirred at the reduced temperature for about five minutes and wherein said second mixture is stirred at the reduced temperature for about one hour.

8. A method according to claim 7 wherein said second mixture is quenched with ammonium chloride and thereafter reduced to a residue.

9. A method according to claim 8 including the step of dissolving said residue in organic solvent not misible in water to form a residue solution after which said residue solution is first washed with water and next washed with brine to form an organic layer.

10. A method according to claim 9 including the steps of removing, drying and recrystallizing said organic layer.

11. A method according to claim 10 wherein recrystalization is accomplished with ethyl acetate/hexane.

12. A method according to claim 2 wherein the step of acylating said 10-deacetyl Baccatin III is accomplished with at least two equivalents of n-butyl lithium and at least two equivalents of benzyl chloroformate.

* * * * *